United States Patent
Borrás Hidalgo et al.

(10) Patent No.: US 10,104,889 B2
(45) Date of Patent: Oct. 23, 2018

(54) METHOD FOR INDUCING RESISTANCE TO DISEASES IN PLANTS

(75) Inventors: Orlando Borrás Hidalgo, Havana (CU); Eduardo Canales López, Havana (CU); Merardo Pujol Ferrer, Havana (CU); Carlos Guillermo Borroto Nordelo, Havana (CU); Yamilet Coll García, Havana (CU)

(73) Assignee: Centro de Ingeniería Genética y Biotecnología, Havana (CU)

( * ) Notice: Subject to any disclaimer, the term of this patent is extended or adjusted under 35 U.S.C. 154(b) by 182 days.

(21) Appl. No.: 14/001,344

(22) PCT Filed: Feb. 27, 2012

(86) PCT No.: PCT/CU2012/000001
§ 371 (c)(1),
(2), (4) Date: Oct. 21, 2013

(87) PCT Pub. No.: WO2012/116664
PCT Pub. Date: Sep. 7, 2012

(65) Prior Publication Data
US 2014/0171326 A1 Jun. 19, 2014

(30) Foreign Application Priority Data
Feb. 28, 2011 (CU) ................... 2011-0046

(51) Int. Cl.
*A01N 49/00* (2006.01)
*A01N 43/22* (2006.01)
*A01N 43/90* (2006.01)
*A01N 65/08* (2009.01)

(52) U.S. Cl.
CPC ............. *A01N 43/22* (2013.01); *A01N 43/90* (2013.01); *A01N 49/00* (2013.01); *A01N 65/08* (2013.01)

(58) Field of Classification Search
CPC ................................ A01N 43/90; A01N 49/00
USPC ........................................................ 504/291
See application file for complete search history.

(56) References Cited

U.S. PATENT DOCUMENTS

| 5,071,466 A * | 12/1991 | Kuraishi | A01N 49/00 504/291 |
| 2010/0009002 A1 * | 1/2010 | Simonetta | A01N 65/28 424/490 |
| 2010/0092442 A1 * | 4/2010 | Jacobsen | A01N 63/00 424/93.46 |

FOREIGN PATENT DOCUMENTS

| DE | 4039017 | 6/1992 |
| EP | 1621629 | 2/2006 |
| WO | 2012053994 | 4/2012 |
| WO | 2012077786 | 6/2012 |

OTHER PUBLICATIONS

Zullo et al. (Plant Growth Regulation, 39: 1-11, 2003).*
Azpiroz et al., An *Arabidopsis* Brassinosteroid-Dependent Mutant is Blocked in Cell Elongation, The Plant Cell, vol. 10, pp. 219-230 (1998).
Bake et al., Signaling in Plant-Microbe Interactions, Science, vol. 276, pp. 726-733 (1997).
J.M. Bove, Huanglongbing: A destructive, newly-emerging, century-old disease of citrus, Journal of Plant Pathology, vol. 88, pp. 7-37 (2006).
Cordelier et al., Biological and molecular comparison between localized and systemic acquired resistance induced in tobacco by a Phytophthora megasperma glycoprotein elicitin, Plant Molecular Biology, vol. 51, pp. 109-118 (2003).
J.V. da Graca, Citrus Greening Disease, Annu. Rev. Phytopathol., vol. 29, pp. 109-136 (1991).
Fritig et al., Antimicrobial proteins in induced plant defense, Current Opinion in Immunology, vol. 10, pp. 16-22 (1998).
Gao et al., Fungal pathogen protection in potato by expression of a plant defensin peptide, Nature America Inc., vol. 18 (2000).
Tim R. Gottwald, Current epidemiological understanding of citrus huanglongbing, Annu. Rev. Phytopathol., vol. 48, pp. 119-139 (2010).
Grove et al., Brassinolide, a plant growth-promoting steroid isolated from *Brassica napus* pollen, Nature, vol. 281, (1979).
Khripach et al., Twenty years of brassinosteroids: Steroidal plant hormones warrant better crops for the XXI century, Annals of Botany, vol. 86, pp. 441-447 (2000).
M. Legrand et al., O-diphenol O-methyltransferases of healthy and tobacco-mosaic-virus-infected hypersensitive tobacco, Planta, vol. 144, pp. 101-108 (1978).
Matsumura et al., Gene expression analysis of plant host-pathogen interactions by SuperSAGE, PNAS, vol. 100, pp. 15718-15723, (2003).
Nakashita et al., Brassinosteroid functions in a broad range of disease resistance in tobacco and rice, The Plant Journal, vol. 33, pp. 887-898 (2003).
Brian J. Staskawicz, Genetics of plant-pathogen interactions specifying plant disease resistance, Plant Physiology, vol. 125, pp. 73-76 (2001).
Zullo et al., Brassinosteroid phytohormones-structure, bioactivity and applications, Braz. J. Plant Physiol., vol. 14, pp. 143-181 (2002).

(Continued)

*Primary Examiner* — Mina Haghighatian
*Assistant Examiner* — Mei Ping Chui
(74) *Attorney, Agent, or Firm* — Hoffmann & Baron, LLP (57) ABSTRACT

The present invention describes a method for the stimulation of the natural defense and the induction of resistance to diseases in plants by simultaneous activation of genes related to the route of the salicylic acid, the jasmonic acid/ethylene and the hypersensitive response. The invention also includes the use of brassinosteroids for the preventive and curative treatment against plant diseases caused by pathogens. In addition, includes a method for the prevention and treatment of the Huanglongbing disease in citrus.

2 Claims, 5 Drawing Sheets
Specification includes a Sequence Listing.

(56) References Cited

OTHER PUBLICATIONS

Gary Lyon, Chapter2: Agents that can elicit induced resistance, Induced Resistance for Plant Defence: A Sustainable Approach to Crop Protection pp. 9-29 (2007).

\* cited by examiner

SEQUENCE LISTING

<160> NUMBER OF SEQ ID NOS: 16

<210> SEQ ID NO 1
<211> LENGTH: 22
<212> TYPE: DNA
<213> ORGANISM: Artificial Sequence
<220> FEATURE:
<223> OTHER INFORMATION: Synthetic sequence

<400> SEQUENCE: 1
tcttcgacgg cataaagaat ca          22

<210> SEQ ID NO 2
<211> LENGTH: 22
<212> TYPE: DNA
<213> ORGANISM: Artificial Sequence
<220> FEATURE:
<223> OTHER INFORMATION: Synthetic sequence

<400> SEQUENCE: 2
ccaaattgag gataagcctt gg          22

<210> SEQ ID NO 3
<211> LENGTH: 22
<212> TYPE: DNA
<213> ORGANISM: Artificial Sequence
<220> FEATURE:
<223> OTHER INFORMATION: Synthetic sequence

<400> SEQUENCE: 3
tcgttggtga ccgtcaaata tc          22

<210> SEQ ID NO 4
<211> LENGTH: 22
<212> TYPE: DNA
<213> ORGANISM: Artificial Sequence
<220> FEATURE:
<223> OTHER INFORMATION: Synthetic sequence

<400> SEQUENCE: 4
tttctccaac gcagcgtaag ta          22

<210> SEQ ID NO 5
<211> LENGTH: 22
<212> TYPE: DNA
<213> ORGANISM: Artificial Sequence
<220> FEATURE:
<223> OTHER INFORMATION: Synthetic sequence

<400> SEQUENCE: 5
aacgggttgc cttcaaatct ta          22

```
<210> SEQ ID NO 6
<211> LENGTH: 22
<212> TYPE: DNA
<213> ORGANISM: Artificial Sequence
<220> FEATURE:
<223> OTHER INFORMATION: Synthetic sequence

<400> SEQUENCE: 6
acatgattgg tgacaggatt gg                                              22

<210> SEQ ID NO 7
<211> LENGTH: 22
<212> TYPE: DNA
<213> ORGANISM: Artificial Sequence
<220> FEATURE:
<223> OTHER INFORMATION: Synthetic sequence

<400> SEQUENCE: 7
cagttgcagt tcttggtgga ac                                              22

<210> SEQ ID NO 8
<211> LENGTH: 22
<212> TYPE: DNA
<213> ORGANISM: Artificial Sequence
<220> FEATURE:
<223> OTHER INFORMATION: Synthetic sequence

<400> SEQUENCE: 8
agaccagaga ggcttcctga aa                                              22

<210> SEQ ID NO 9
<211> LENGTH: 19
<212> TYPE: DNA
<213> ORGANISM: Artificial Sequence
<220> FEATURE:
<223> OTHER INFORMATION: Synthetic sequence

<400> SEQUENCE: 9
ccacacttgg ctcggatgc                                                  19

<210> SEQ ID NO 10
<211> LENGTH: 18
<212> TYPE: DNA
<213> ORGANISM: Artificial Sequence
<220> FEATURE:
<223> OTHER INFORMATION: Synthetic sequence

<400> SEQUENCE: 10
cgtgcggagc aatggttc                                                   18

<210> SEQ ID NO 11
<211> LENGTH: 22
<212> TYPE: DNA
<213> ORGANISM: Artificial Sequence
<220> FEATURE:
<223> OTHER INFORMATION: Synthetic sequence

<400> SEQUENCE: 11
gaatgttgtt gagcgttatg cc                                              22

<210> SEQ ID NO 12
<211> LENGTH: 23
<212> TYPE: DNA
<213> ORGANISM: Artificial Sequence
<220> FEATURE:
<223> OTHER INFORMATION: Synthetic sequence
```

```
<400> SEQUENCE: 12
agctgatcat gcaagttgta gca                                    23

<210> SEQ ID NO 13
<211> LENGTH: 20
<212> TYPE: DNA
<213> ORGANISM: Artificial Sequence
<220> FEATURE:
<223> OTHER INFORMATION: Synthetic sequence

<400> SEQUENCE: 13
gtggctccac cagagagaaa                                        20

<210> SEQ ID NO 14
<211> LENGTH: 20
<212> TYPE: DNA
<213> ORGANISM: Artificial Sequence
<220> FEATURE:
<223> OTHER INFORMATION: Synthetic sequence

<400> SEQUENCE: 14
tggatggacc agactcatca                                        20

<210> SEQ ID NO 15
<211> LENGTH: 21
<212> TYPE: DNA
<213> ORGANISM: Artificial Sequence
<220> FEATURE:
<223> OTHER INFORMATION: Synthetic sequence

<400> SEQUENCE: 15
ctaatcccca aaagccatct c                                      21

<210> SEQ ID NO 16
<211> LENGTH: 20
<212> TYPE: DNA
<213> ORGANISM: Artificial Sequence
<220> FEATURE:
<223> OTHER INFORMATION: Synthetic sequence

<400> SEQUENCE: 16
cttcaggcaa aaccaactcc                                        20
```

METHOD FOR INDUCING RESISTANCE TO DISEASES IN PLANTS

This application claims priority based on an International Application filed under the Patent Cooperation Treaty, PCT/CU2012/000001, filed Feb. 27, 2012, which claims priority from Cuban Application No. 2011-0046, filed Feb. 28, 2011, each of which are incorporated herein by reference.

FIELD OF THE INVENTION

The present invention is related to the agricultural biotechnology field, specifically to the stimulation of the natural defense and the induction of resistance to diseases in plants, to avoid or to fight the diseases caused by pathogens.

PREVIOUS ART

In recent decades many studies have been made about plant—pathogen interactions, from morphological, physiological, biochemical and molecular point of view. However, the results achieved to date do not meet the needs and knowledge of the major research groups in the world, and high yields through a stable and efficient protection of crops is not accomplish. Despite the numerous measures taken globally for an integrated crops protection, major crop losses from disease reaching 80% of production are reported each year, specifically in situations where epidemics occur (Gao et al. (2000) Nature Biotechnol. 18: 1307-1310).

Plants and pathogens have co-evolved over millions of years. During this interaction, strategies have emerged that allow plants to recognize potential invading pathogens and trigger a successful defense. Likewise, pathogens have developed mechanisms that enable them to evade and/or suppress plant defense responses. The influence of this selective pressure on plants has led to the improvement of their defense mechanisms. As a result, the success of the pathogen to cause disease, far from being the rule is an exception (Staskawicz (2001) Plant Physiology 125: 73-76).

The perception of specific and general elicitors by plants not only allows the recognition of pathogens, but allows the transduction of signals for the activation of response mechanisms. Among the various signaling pathways activated are those mediated by intermediates such as reactive oxygen, salicylic acid, ethylene and jasmonic acid. The crossover between these phytohormones signaling pathways provides a regulatory potential that allow activation of an optimal combination of responses depending on the specific pathogen. The expression of genes related to pathogenicity (PR) and the synthesis of antimicrobial compounds that are generally phytoalexins, defensins, phenolics and flavonoids produced to directly attack the pathogen are also activated (Baker et al. (1997) Science 276: 726-733).

There are other response mechanisms that operate in plants, whose effects persist for a relatively long period of time after infection. These are called: acquired localized response and systemic acquired response. Acquired localized response is observed in a ring of cells, 5-10 mm thick, about injuries caused by the hypersensitive response. This area is characterized by a large accumulation of pathogenesis-related proteins, mainly basic (Fritig et al. (1998) Current Opinion of Immunology 10: 16-22) and stimulation of enzymes such as methyltransferases (Legrand et al. (1978) Planta 144: 101-108), the phenylpropanoid pathway, which is involved in the production of antibiotics such as scopoletin, which does not provide a suitable environment for pathogens, preventing their spread throughout the plant. Systemic acquired response gives the plant a higher level of resistance against a subsequent infection of the same pathogen. It develops not only in infected tissues, but throughout the plant. It is characterized by the accumulation of PR proteins, particularly acidic, which are related to the signaling mechanism of salicylic acid (Cordelier et al. (2003) Plant Molecular Biology 51: 109-118).

Plants have the ability to synthesize a variety of steroids that function as hormones. However, it was not until 1979 that the presence of steroid hormones was confirmed in plants. In that year, American scientists published data on a new steroidal lactone called brassinolide, which was isolated from *Brassica napus* L. pollen (Grove et al. (1979) Nature 281: 216-217). The brassinosteroids have been recognized as a new class of phytohormones that play an important role in growth regulation (Azpiroz et al. (1998) Plant Cell 10: 219-230). The physiological properties of brassinosteroids allow us to consider them as very promising for use without impacting the environment. Natural substances may be suitable for wide application in plant protection and promotion of efficiency in agriculture.

From the beginning the brassinosteroids were considered promising compounds for application in agriculture because they showed different types of regulatory activity in the growth and development of plants, and its economic value as an advocate of performance (Khripach et al. (2000) Ann. Botany 86: 441-447). An important feature is the ability of brassinosteroids to act in extremely low concentrations. An indirect confirmation of this phenomenon is the low concentration of brassinosteroids in plants. A typical amount for use in agriculture is between 5 and 50 mg per hectare for growing plants (Khripach et al. (2000) Ann. Botany 86: 441-447).

The brassinosteroids can also play a role in the response of plants to pathogens. Resistance to bacterial and fungal pathogens have been induced by brassinosteroids in rice and tobacco, this resistance was not correlated with increased accumulation of salicylic acid or increased expression of genes associated with systemic acquired resistance (Nakashita et al. (2003) Plant Journal 33: 887-898).

The "Huanglongbing" (HLB) caused by the bacterium *Candidatus 'Liberibacter asiaticus'* is the most destructive disease of citrus worldwide by the severity of symptoms, the speed with which it spreads and affects all commercial citrus species. It is a disease that still has no cure (Gottwald (2010) Annu. Rev. Phytopathol. 48: 6.1-6.21). The disease was first detected in Asia in the late nineteenth century, and then its presence was reported in South Africa in the early twentieth century, which helped the spreading in both continents through the years (Gottwald (2010) Annu. Rev. Phytopathol. 48: 6.1-6.21). Currently three variants of the disease are recognized (Asian, African and American). The causal organism is a "fastidious" gram-negative bacterium, which can not be obtained in pure culture on artificial media. This organism is restricted to the phloem of Rutaceae, although it has the ability to multiply in the hemolymph and salivary glands of the psyllid vectors (Asian citrus psyllid—*Diaphorina citri*). In insects, it penetrates the intestinal wall to reach the salivary glands, via hemolymph in a period of 1 to 3 weeks depending on the virulence of the strain.

Symptoms vary with the variety and age of the affected plant, as these are clearly observed in young and vigorous trees, while those affected after development, present less marked symptoms. In matured leaves, the tissues along the midrib and secondary veins become yellow and chlorosis spreads on the lateral veins until the leaf falls (da Graca (1991) Annu. Rev. Phytopathol. 29:109-36). The process is more severe in young leaves, which remain small in size. Plants show a considerable defoliation with apical death a few years after infection, mottling and yellowing are also generalized. They develop multiple shoots with small leaves, pale and mottled. During the infection there is a poor fruit set, early dropping of these and those who remain on the tree are small and asymmetric, taking the correct color only the side expose to sunlight, while the other side takes an intense olive-green coloration (Bové J (2006) Plant Pathol. 88: 7-37). The fruits have a low amount of juice, and a low concentration of soluble solids and sugars, becoming highly acidic and not suitable to be used in industry (Gottwald (2010) Annu. Rev. Phytopathol. 48: 6.1-6.21).

The economic impact for the presence of HLB in citrus— producing countries has increased year by year, with losses estimated in about a 30-100%, due to reduced yields and fruit quality. Until now, there is no region in the world where the HLB is adequately controlled and the disease does not exist, which contributes to increase its severity and incidence (Gottwald (2010) Annu. Rev. Phytopathol. 48: 6.1-6.21). Recently, the use of systemic acquired resistance have been evaluated by using compounds such as salicylic acid and phosphite in combination with micronutrients to maintain HLB-infected trees in a productive state. However, in some cases, there was not a significant difference between treated and untreated trees, in relation to the decrease of HLB, fruit drop, yield and quality (Gottwald (2010) Annu. Rev. Phytopathol. 48: 6.1-6.21).

Therefore, an important problem that remains in agriculture is the control of plant diseases, which limit agricultural production each year worldwide.

DETAILED DESCRIPTION OF THE INVENTION

This invention helps to solve the above mentioned problem by providing an effective method for stimulating the natural defense and the induction of resistance to diseases in plants, by applying a compound that simultaneously activate genes related to the route of salicylic acid, jasmonic acid/ethylene and hypersensitive response in them.

Induction of resistance to diseases is a method of great importance and interest at present, which allows the use of biochemical and molecular mechanisms that already exist in the plant for use in disease control. The defense of plants to diseases comprises a series of events related to the recognition, signaling and response defined as innate immunity in plants. This innate immunity can be activated by a number of factors, which decisively contribute to the disease control. Among the defense mechanisms that are activated by the plant is the synthesis of antimicrobial phytoalexins, defensins and pathogenesis-related proteins. These responses are mediated by activation of genes related to salicylic acid, jasmonic acid/ethylene and hypersensitive response.

In the present invention is achieved, for the first time, the simultaneous activation of enzymes chitinase, beta 1, 3 glucanase, glutathione peroxidase, phenylalanine ammonia lyase, superoxide dismutase, and allene oxide synthase, which are part of the signaling pathways of salicylic acid, jasmonic acid/ethylene and the hypersensitive response. This activation correlates with protection against bacteria, oomycetes and fungi.

Additionally, we demonstrate the simultaneous activation of a group of new genes, belonging to the route of salicylic acid, jasmonic acid/ethylene and hypersensitive response, whose activation correlates with protection against bacteria, oomycetes and fungi. These genes were identified and characterized by the technique of Serial Analysis of Gene Expression (SuperSAGE). It is surprising, having into account the prior state of the art, that the activation of genes that belong to the pathway of the salicylic acid, the jasmonic acid/ethylene and the hypersensitive response occur simultaneously in response to the application of a natural compound.

In the context of the invention said compound can be a phytohormone, a nucleic acid, a lipid or a peptide, among other compounds.

In one embodiment of the invention, the stimulation of the natural defense and the induction of resistance to diseases in plants by simultaneous activation of genes associated with salicylic acid, jasmonic acid/ethylene and hypersensitive response, occurs after the application of phytohormones to such plants. In a particular embodiment, the phytohormone is a natural brassinosteroid or its analogue. In the context of this invention it is considered an analogue of brassinosteroid such compound that is synthesized starting from changes in the structure of the rings of a natural brassinosteroid in order to increase its activity.

The method disclosed in this invention allows the preventive and curative treatment of plant diseases caused by bacteria, oomycetes and fungi through the simultaneous activation of genes related to the route of salicylic acid, jasmonic acid/ethylene and hypersensitive response. In one embodiment of the invention, the disease being treated or prevented is the "Huanglongbing" (HLB), produced by the bacterium *Candidatus 'Liberibacter asiaticus*' in citrus. In another embodiment, the disease that is treated or prevented is that caused by *Alternaria solani* in the tomato cultures, or that caused by *Phytophthora parasitica* in tobacco cultures.

The present invention also discloses for the first time, the concentration and application frequency of the natural brassinosteroids (and their analogues) to allow the effective control of plant diseases. In one embodiment of the invention, the application of the natural brassinosteroid or analogue, in a concentration range from 0.01 to 20 µM, allows drastic reduction of the agents that cause diseases of bacterial and fungal origin, by reducing the number of copies of the bacterium, oomycetes or fungus, through the treatment of sick plants. The method proposed in the present invention can be used to prevent the infection of healthy plants by periodically applying a natural brassinosteroid and its analogue. In a particular embodiment of the invention, the application of the brassinosteroid to the plant occurs at least once in a month. In another embodiment, the application of the brassinosteroid to the sick plants occurs with a frequency of at least twice in a month. The range of brassinosteroid concentration to be applied, both for natural and analogue, varies depending on the crop to be protected or treated, and also depending on the application technology. As known by those skilled in this technical field, the effective concentrations of the compound may considerably decrease when a Low Volume Application or Ultra-Low Volume Application is used.

In one embodiment of the invention, the method of stimulating the natural defense and inducing resistance to diseases in plants involves the application of a brassinosteroid or an analogue in combination with a pesticide.

Another object of the present invention is a composition for stimulating the natural defense and inducing resistance to diseases in plants comprising a compound that simultaneously activates genes related to the route of the salicylic acid, the jasmonic acid/ethylene and the hypersensitivity response, and wherein said compound is a phytohormone.

In a preferred embodiment, said composition comprises a natural brassinosteroid or a brassinosteroid analogue. In a particular embodiment of the invention, the natural brassinosteroids and the analogues are obtained by chemical synthesis. For the purpose of the invention, the brassinosteroids can be formulated through a solution, suspension, emulsion, powder, granule, concentrate emulsifiable, aerosol, impregnated granule, adjuvant, paste or through encapsulations.

In one embodiment of the invention, in the composition for preventing or curing plant diseases, the natural brassinosteroid or the brassinosteroid analogue is in a range between 0.01 to 20 µM, or its equivalent for use in low or ultra-low volume. Another object of the present invention is the use of a brassinosteroid to prepare a composition for the stimulation of the natural defense and the induction of resistance to diseases in plants, where the composition is periodically applied. In one embodiment of the invention the plant diseases that can be prevented or treated by this new use of the brassinosteroids are caused by a bacterium, a fungus or oomycete.

Another aspect of the present invention relates to a method for the prevention or treatment of the Huanglongbing (HLB) disease in citrus where a brassinosteroid is periodically applied to the plant, at least once a month. In said method the brassinosteroid can be a natural compound or a brassinosteroid analogue.

EXAMPLES

Example 1. Simultaneous Activation of Genes Related to the Natural Resistance of Plants to Diseases after the Treatment with a Brassinosteroid Analogue Citrus plants (*Citrus sinensis*) were treated with the brassinosteroid analogue (25R)-3-hydroxy-C-homo-11-oxa-5-espirostan-12-one at 20 µM (Iglesias et al. (1998) Synthetic Communications 28: 75-81). Leaves from five plants were collected at 0, 1, 5, 10, 24 and 48 hours after spray application. Total RNA was extracted from leaves using the RNeasy kit (Qiagen, Valencia, Calif.) according to manufacturer's instructions, which includes a DNase treatment. The cDNAs were synthesized by using oligo-dT primer and reverse transcription kit SuperScript III (Invitrogen, Carlsbad, Calif.) according to manufacturer's instructions. The real-time quantitative PCR was performed using a Rotor-Gene 3000 PCR machine (Corbett, Australia) and QuantiTect SYBR Green PCR kit (Qiagen). All sequences of primers for genes related to defense against diseases of citrus plants are shown in Table 1. The reaction conditions in real-time PCR were: an initial denaturation step at 95° C. for 15 min. followed by denaturation at 95° C. for 15 s, an alignment step for 30 s at 60° C. and an extension step for 30 s at 72° C. for 40 cycles. The analysis was carried out using the RotorGene 3000 software (Corbett, Australia) and five replicates were used for each sample. Experiments were repeated twice.

TABLE 1

List of oligonucleotides used in the experiments.

| *Citrus sinensis* genes analyzed | Oligonucleotides |
|---|---|
| quitinase | 5'-TCTTCGACGGCATAAAGAATCA-3' SEQ ID NO. 1 <br> 5'-CCAAATTGAGGATAAGCCTTGG-3' SEQ ID NO. 2 |
| beta-1,3-glucanase | 5'-TCGTTGGTGACCGTCAAATATC-3' SEQ ID NO. 3 <br> 5'-TTTCTCCAACGCAGCGTAAGTA-3' SEQ ID NO. 4 |
| Phenylalanine ammonia-lyase | 5'-AACGGGTTGCCTTCAAATCTTA-3' SEQ ID NO. 5 <br> 5'-ACATGATTGGTGACAGGATTGG-3' SEQ ID NO. 6 |

TABLE 1 -continued

List of oligonucleotides used in the experiments.

| Citrus sinensis genes analyzed | Oligonucleotides |
|---|---|
| superoxide dismutase | 5'-CAGTTGCAGTTCTTGGTGGAAC-3' SEQ ID NO. 7 <br> 5'-AGACCAGAGAGGCTTCCTGAAA-3' SEQ ID NO. 8 |
| allene oxide synthase | 5'-CCACACTTGGCTCGGATGC-3' SEQ ID NO. 9 <br> 5'-CGTGCGGAGCAATGGTTC-3' SEQ ID NO. 10 |
| glutathione peroxidase | 5'-GAATGTTGTTGAGCGTTATGCC-3' SEQ ID NO. 11 <br> 5'-AGCTGATCATGCAAGTTGTAGCA-3' SEQ ID NO. 12 |
| actin | 5'-GTGGCTCCACCAGAGAGAAA-3' SEQ ID NO. 13 <br> 5'-TGGATGGACCAGACTCATCA-3' SEQ ID NO. 14 |

Figure 1:
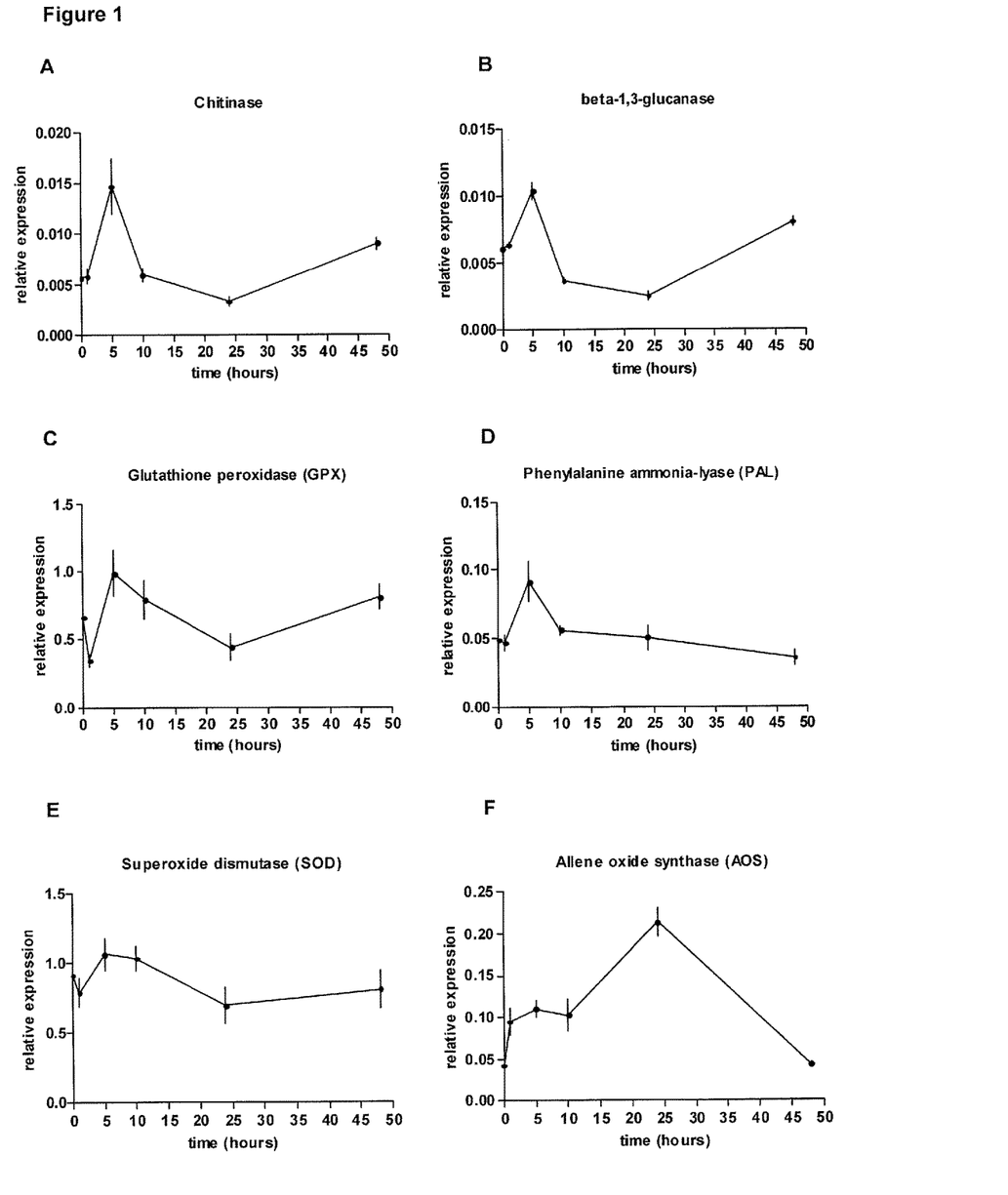
FIG. 1. Relative expression of genes related to defense responses to diseases in citrus plants treated with the brassinosteroid analogue (25R)-3-hydroxy-C-homo-11-oxa-5-espirostan-12-one. It shows the relative expression of genes encoding for: chitinase (A), β-1,3-glucanase (B), gluthatione peroxidase (C), phenylalanine-ammonia lyase (D), superoxide dismutase (E), alene oxide synthase (F). The bars on the curves represent the standard deviation of the mean of 10 plants for each time tested. The genes tested are related to the resistance of plants through the salicylic acid, jasmonic acid/ethylene and hypersensitivity response.

FIG. 1 shows as all analyzed genes were activated after treatment of citrus plants with the brassinosteroid analogue. Allene oxide synthase gene had the highest level of expression at 24 hours, while the rest of the genes had their highest expression at 5 hours after analogue was applied. This group of genes has an important role in plant defense against pathogens.

Figure 2:
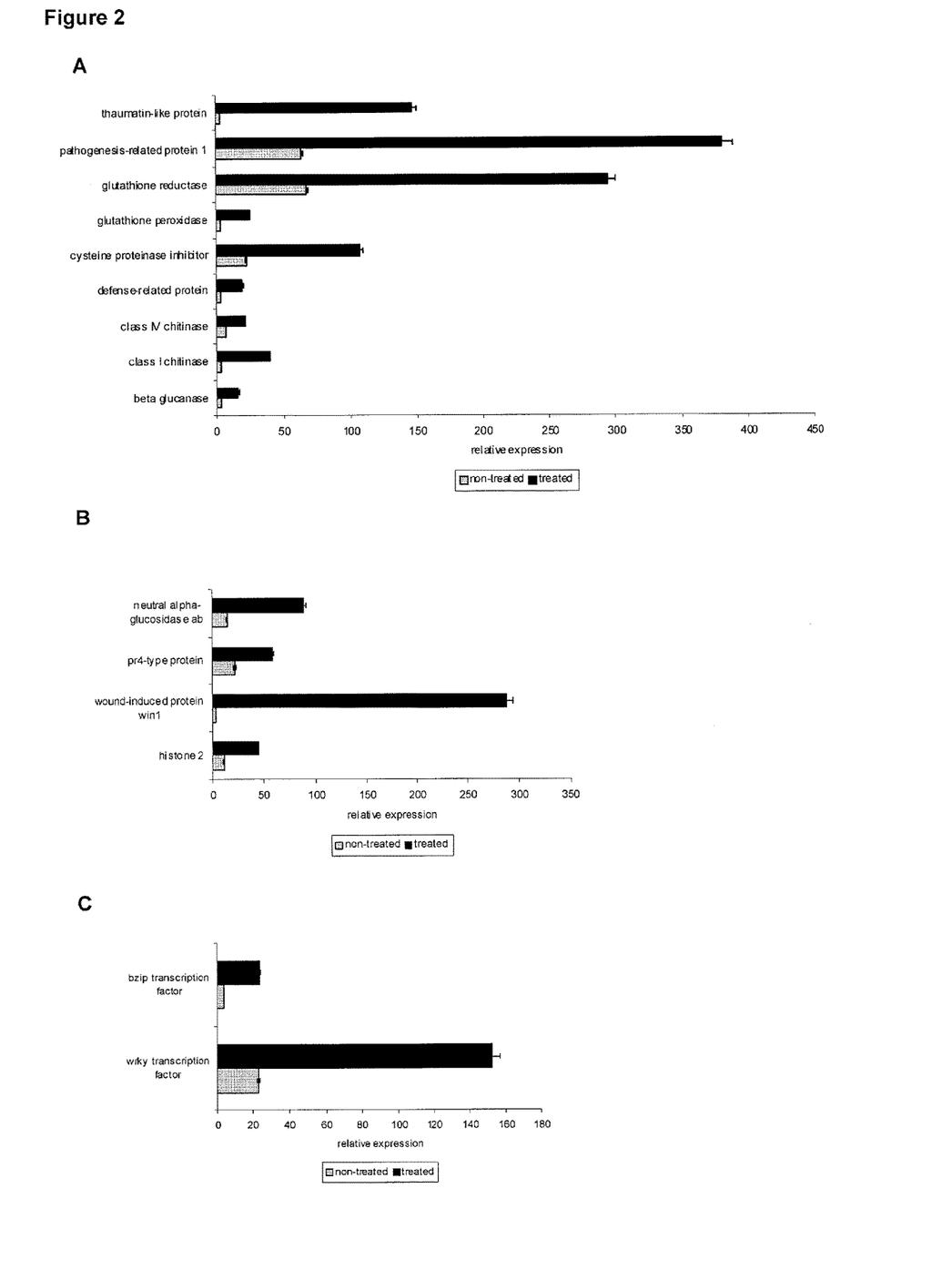
FIG. 2. Relative expression of new genes identified by the SuperSAGE technique, activated during the treatments with an analogous of brassinosteroid. The bars represent the standard deviations of the mean of 10 leaves per plant in each time points. The genes were grouped in the following categories: genes related with the defense response in plants against pathogens in general (A); genes related with the defense response in plants against bacterium (B); transcription factors related with the plant defense against disease (C); signaling to defense response (D); and genes related with the phytoalexin biosynthesis (E).
Figure 3:
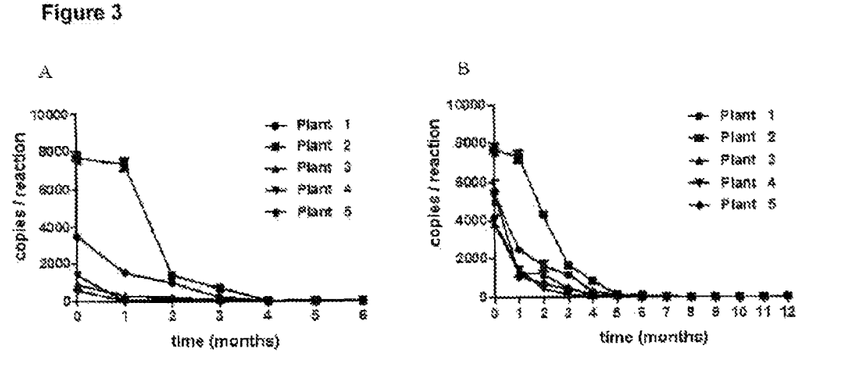
FIG. 3. Effect of a brassinosteroid analogue on the reduction of HLB in citrus plants in development (A) and adult (B), measured as copies of the HLB bacterium per reaction, determined by polymerase chain reaction (PCR). The bars on the curves represent the standard deviation of the mean of 10 leaves for each time tested.

Example 2. Identification of New Genes Related to the Natural Defense Response in Plants Treated with a Brassinosteroid Analogue Citrus plants (*Citrus sinensis*) were treated with the brassinosteroid analogue (25R)-3-hydroxy-C-homo-11-oxa-5-espirostan-12-one at 20 µM. Leaves from five plants were collected at 1, 5, 10, 24 and 48 hours after spray application. Total RNA was extracted from leaves using the RNeasy kit (Qiagen, Valencia, Calif.) according to manufacturer's instructions. The cDNAs were synthesized by using biotinylated oligo-dT primer and reverse transcription kit SuperScript III (Invitrogen, Carlsbad, Calif.) according to manufacturer's instructions. Samples of five citrus plants treated with water and collected during the times listed above were used as control. The identification and characterization of new genes was performed by the construction of two cDNA libraries by the technique of SuperSAGE (Matsumura et al. (2003) PNAS 100: 15718-15723). The control library was the mixture of leaves of plants treated with water at different times and target sample was the mixture of citrus plant leaves treated with the analogue at different times. The new genes related to plant response to the HLB, activated by application of brassinosteroid analogue, were isolated, sequenced and analyzed. FIG. 2 shows the new genes activated by the analogue, which are related to the natural defense mechanism of plants against diseases. Importantly, as this analogue of brassinosteroids simultaneously activates genes related to hypersensitive response, salicylic acid and jasmonic acid/ethylene, this is a new mechanism so far not described.

Example 3. Evaluation of the Effect of the Application of a Brassinosteroid Analogue on the Control of HLB of Citrus in Plants in the Development Phase and in Adult Plants a) Evaluation of the Effect on Citrus Plants in the Development Phase.

Figure 4:
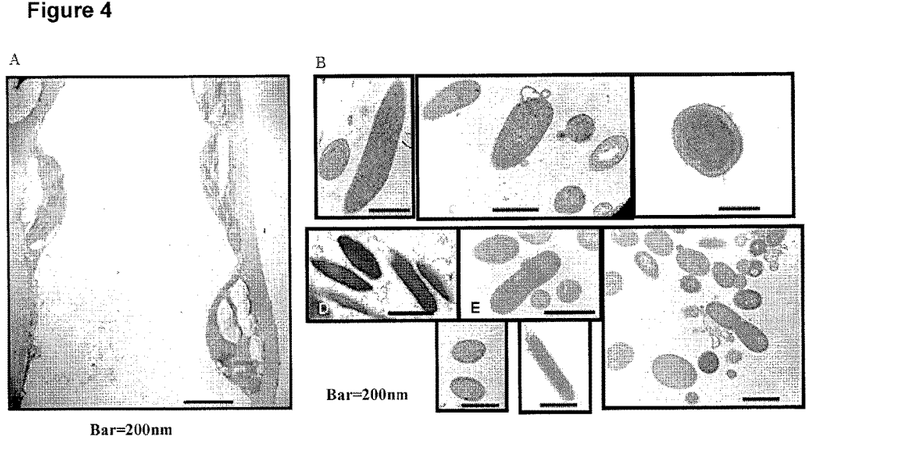
FIG. 4. Electron microscopy of leaves from HLB infected plants treated (A) and untreated (B) with a brassinosteroid analogue. Twenty electron micrographs were made for each sample analyzed at different magnifications. We studied a total of 10 grids per sample. Each copper grid has 400 holes for viewing.
Figure 5:
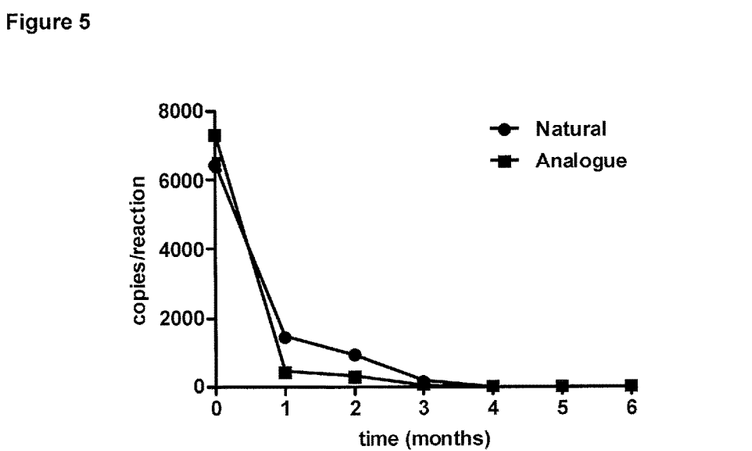
FIG. 5. Evaluation of the effect of natural brassinosteroid and analogue on the reduction of HLB, measured as copies of the HLB bacterium per reaction. The bars on the curves represent the standard deviation of the mean of 10 plants for each time tested.
Figure 6:
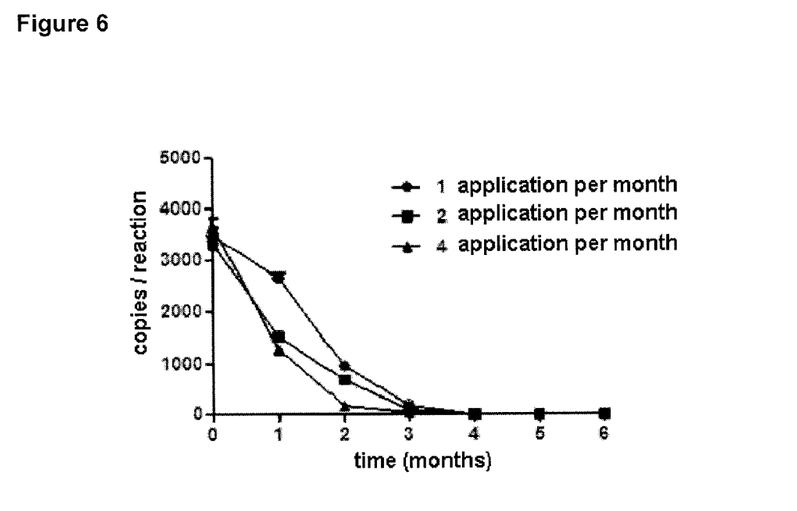
FIG. 6. Effect of the frequency of application of brassinosteroid analogue (25R)-3-hydroxy-C-homo-11-oxa-5-espirostan-12-one on reducing HLB, measured as copies of the HLB bacterium per PCR reaction. The bars on the curves represent the standard deviation of the mean of 10 leaves per plant for each time tested.
Figure 7:
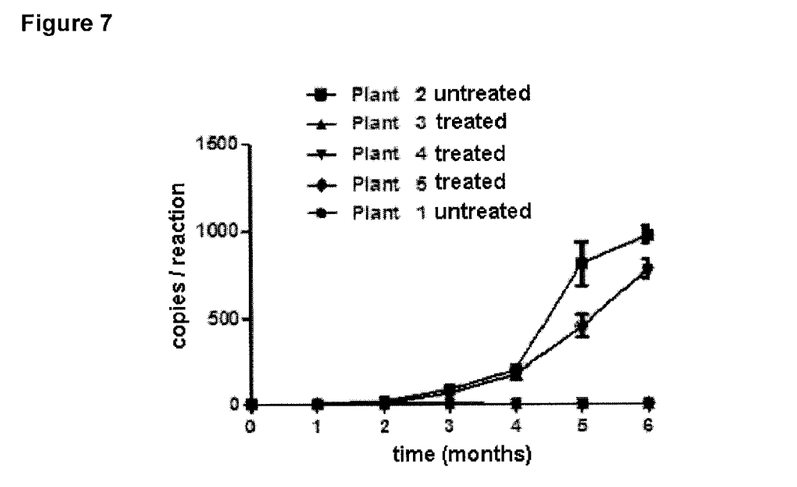
FIG. 7. Protective effect of brassinosteroid analogue (25R)-3-hydroxy-C-homo-11-oxa-5-espirostan-12-one on HLB of citrus, measured as copies of the HLB bacterium per PCR reaction. Product applications were made once a month. The bars on the curves represent the standard deviation of the mean of 10 leaves per plant for each time tested.

The experiment was developed under conditions of greenhouses. Plants (*Citrus sinensis*) with symptoms of HLB were placed in black plastic bags with a suitable irrigation regimen. The levels of the bacteria *Candidatus 'Liberibacter asiaticus'* in plants with symptoms of HLB were determined by real-time PCR, through the absolute quantification of bacteria (copies of bacteria per reaction) in the leaves according to the standard curve and 16S ribosomal DNA amplified from the bacteria. Quantification of bacteria was evaluated every month for 6 months. The last assessment was developed by taking all the leaves of the plant and performing a mixture prior to isolation of DNA. The concentration of the brassinosteroid analogue (25R)-3-hydroxy-C-homo-11-oxa-5-espirostan-12-one was 20 μM and was applied by spraying every 15 days. The DNA was extracted from leaves according to the protocol for isolation of DNA from Promega. The real-time quantitative PCR was performed using a RotorGene 3000 PCR machine (Corbett, Australia) and QuantiTect SYBR Green PCR kit (Qiagen). The oligos used for quantification of bacteria were: CTAATCCCCAAAAGCCATCTC SEQ ID NO. 15 and CTTCAGGCAAAACCAACTCC SEQ ID NO. 16. The reaction conditions in real-time PCR were: an initial denaturation step at 95° C. for 15 min. followed by denaturation at 95° C. for 15 s, an alignment step for 30 s at 60° C. and an extension step for 30 s at 72° C. for 40 cycles. The analysis was carried out using the RotorGene 3000 software (Corbett, Australia) and five replicates were used for each sample. Experiments were repeated twice. As controls, sick citrus plants were used, to which the brassinosteroid was not applied. As there was a significant reduction in levels of bacteria from the month, reaching undetectable levels from month 4, the last evaluation, at the end the experiment As shown in FIG. 3A, there was a significant reduction in levels of bacteria from the second month, reaching undetectable levels from month 4, which was maintained until the last evaluation, conducted at the end of the experiment. Importantly, this behavior was observed in all plants that were treated with this analogue of brassinosteroid.

b) Evaluation of the Effect on Adult Citrus Plants.

The experiment was developed under natural conditions. The levels of the bacteria *Candidatus 'Liberibacter asiaticus'* in 30 plants with symptoms of HLB were determined by real-time PCR, through the absolute quantification of bacteria (copies of bacteria per reaction) in the leaves according to the standard curve and 16S ribosomal DNA amplified from the bacteria. Quantification of bacteria was evaluated every month for a year. The last assessment was developed by taking all the leaves of the plant and performing a mixture prior to DNA isolation. The concentration of the brassinosteroid analogue (25R)-3-hydroxy-C-homo-11-oxa-5-espirostan-12-one was 20 mM and was applied by spraying every 15 days. DNA was extracted from leaves according to the protocol for isolation of DNA from Promega. The real-time quantitative PCR was performed as described in Example 3a. Diseased citrus plants, to which the brassinosteroid was not applied, were used as controls. As shown in FIG. 3B, there was a significant reduction in bacteria levels from third months, reaching undetectable levels from months 8, a pattern that continued until the last evaluation, conducted at the end of experiment. All plants that were treated with this analogue of brassinosteroid reduced levels of bacteria.

c) Electron Microscopy of Treated Citrus Plants.

The objective of this experiment was the diagnosis of the bacterium *Candidatus 'Liberibacter asiaticus'* through an ultrastructural study by transmission electron microscopy in HLB infected citrus plants (*Citrus sinensis*), treated with the same analogue of brassinosteroid. Leaf samples were taken from HLB (*Candidatus 'Liberibacter asiaticus'*) infected citrus plants, treated for one year. As a control, leaf samples were taken from infected plant without application of the product. The different samples were fixed in glutaraldehyde 5% overnight under vacuum at 4° C. and post-fixed in 1% osmium tetroxide for 12 hours at 4° C. Subsequently, the samples were washed in cacodylate buffer pH 7.4 and dehydrated in increasing concentrations of acetone (20, 30, 40, 50, 60, 70, 80, 90 and 100%) for 15 minutes each time at 4° C., except 100% that took place at room temperature for 1 hour. The inclusion was made with low viscosity. The ultrathin sections were made with an ultramicrotome (NOVA, LKB) with a thickness of 40-50 nm, and were placed on copper grids of 400 holes. Then, the grids were contrasted with saturated uranyl acetate and lead citrate and examined with a JEOL JEM 2000 EX (JEOL). 20 electron micrographs were made for each sample analyzed at different magnifications. We studied a total of 10 grids per sample. Each copper grid has 400 holes for viewing. In treated samples the presence of bacteria was not observed (FIG. 4A), whereas in the untreated citrus leaves (control) the presence of longitudinal and transverse bacteria *Candidatus 'Liberibacter asiaticus'* was observed at the ultrastructural level (FIG. 4B).

Example 4. Evaluation of Different Concentrations of the Brassinosteroid Analogue (25R)-3-Hydroxy-C-Homo-11-Oxa-5-Espirostan-12-One in the Control of Citrus HLB The objective of this experiment was to assess the minimum concentration needed of the brassinosteroid analogue (25R)-3-hydroxy-C-homo-11-oxa-5-espirostan-12-one to control citrus HLB. Five citrus plants (*Citrus sinensis*) with HLB were used, for each concentration of the analogue. Concentrations tested were 0.001, 0.01, 0.1, 1, 5, 10, 20, 40, 60 μM, and it was applied by spraying every 15 days for 6 months. The evaluation was performed 6 months after treatment. The levels of the bacteria *Candidatus 'Liberibacter asiaticus'* were determined according to example 3a. As shown in Table 2, from the concentrations of 0.01 and up to 60 μM of brassinosteroid analogue, bacteria levels were drastically reduced.

TABLE 2

Effect of different concentrations of the brassinosteroid analogue (25R)-3-hydroxy-C-homo-11-oxa-5-espirostan-12-one on bacteria.

| Concentration of the brassinosteroid analogue (μM) | Absolute concentration of the bacterium after 6 months of treatment (Copies of the bacteria by reaction) |
|---|---|
| 0 | 2788 |
| 0.001 | 522 |
| 0.01 | 29 |
| 1 | 1 |
| 5 | 0 |
| 10 | 0 |
| 20 | 0 |
| 40 | 0 |
| 60 | 0 |

Example 5. Evaluation of the Effect of the Application of a Natural Brassinosteroid (Brassinolide) and a Brassinosteroid Analogue in the Control of Citrus HLB In order to evaluate the effect of a natural brassinosteroid (brassinolide) (Khripach et al. (2000) Ann. Botany 86: 441-447) and the brassinosteroid analogue (25R)-3-hydroxy-C-homo-11-oxa-5-espirostan-12-one in the control of HLB in the same experiment, 10 HLB infected citrus plants were used for each treatment. Both compounds were applied by spray at a concentration of 1 μM every 15 days for 6 months. The levels of the bacteria *Candidatus 'Liberibacter asiaticus'* were determined according to Example 3a. FIG. 5 shows how both the natural and analog compound had a positive effect in achieving a significant reduction in bacteria levels during the evaluation period.

Example 6. Evaluation of the Effect of the Application Frequency of a Brassinosteroid Analogue on the Control of Citrus HLB The objective of this experiment was to determine the influence of frequency of spray application of brassinosteroid analogue (25R)-3-hydroxy-C-homo-11-oxa-5-espirostan-12-one in the control of HLB in diseased citrus plants. Five plants were used per treatment and application frequencies were 1, 2 and 4 times per month. Analogue concentration used was 1 μM and the determinations of the bacterium level were performed every month until the sixth month. The levels of the bacteria *Candidatus 'Liberibacter asiaticus'* were determined according to Example 3a. As shown in FIG. 6, bacterial reduction was observed in all tested variants. The compound application two times a month and weekly significantly reduced levels of bacteria, more early, compared with a single application per month.

Example 7. Evaluation of the Preventive Effect of a Brassinosteroid Analogue on Citrus HLB This experiment was developed to determine the preventive effect of applying the analog (25R)-3-hydroxy-C-homo-11-oxa-5-espirostan-12-one twice a month at a concentration of 1 μM on citrus plants without HLB in an area with citrus plants with HLB and high vector insect populations (Asian citrus psyllid—*Diaphorina citri*). Ten leaves were spray-applied the analogue, and other 10 leaves were used without product application. The levels of the bacteria *Candidatus 'Liberibacter asiaticus'* were determined according to example 3a. As shown in FIG. 7, the analogous application of citrus plants without HLB allowed to protect them against infection from bacteria through the vector, while the plants to which the analogous was not applied, as the months passed, were increasing levels of bacteria and symptoms of HLB. This was another surprising and unexpected result, which allows the use of this method for the protection of citrus against this important disease.

Example 8. Evaluation of the Effect of the Application of a Natural Brassinosteroid and an Analogue on the Control of Other Plant Diseases In order to evaluate the effect of the brassinosteroid analogue (25R)-3-hydroxy-C-homo-11-oxa-5-espirostan-12-one and a natural brassinosteroid (brassinolide), on the control of other plant diseases, experiments were conducted with tobacco and tomato plants inoculated with *Phytophthora parasitica* and *Alternaria solani*, respectively. Both the natural brassinosteroid as the analogue were applied by spraying at a concentration of 1 μM every 15 days for 3 months. The mortality rate was determined at 3 months. Table 3 shows how both brassinosteroids had a marked effect in reducing the incidence of diseases caused by these pathogens. Hundred plants were used for each treatment. Untreated plants were used as controls.

TABLE 3

Effect of natural brassinosteroid and an analogue in the control of diseases caused by oomycetes and fungi.

| Pathogen/plant | Control * | Natural brassinosteroid | Brassinosteroid analogue |
|---|---|---|---|
| *Alternaria solani*/tomato | 84 | 12 | 9 |
| *Phytophthora parasitica*/tobacco | 81 | 13 | 11 |

* Values represent the percentage of mortality due to diseases caused by these pathogens.

The invention claimed is:

1. A method for the treatment of Huanglongbing (HLB) disease in citrus plants in need thereof, said method comprising applying to said plants a composition for the activation of genes associated with salicylic acid, jasmonic acid/ethylene and hypersensitive response, said composition consisting of a brassinosteroid.

2. The method of claim 1 wherein the brassinosteroid is a natural brassinosteroid compound or an analogue thereof, wherein the natural brassinosteroid compound or analogue thereof is applied at a concentration of 0.01-20 µM at least once a month, and wherein the natural brassinosteroid is brassinolide and the brassinosteroid analogue is (25R)-3-hydroxy-C-homo-11-oxa-5-espirostan-12-one.

* * * * *